United States Patent [19]

Rey

[11] Patent Number: Plant 7,240

[45] Date of Patent: Jun. 5, 1990

[54] ELM TREE NAMED GOLDEN REY ELM

[75] Inventor: Bruce Rey, Oklahoma City, Okla.

[73] Assignee: Preston Warren, Spencer, Okla.

[21] Appl. No.: 318,745

[22] Filed: Mar. 3, 1989

[51] Int. Cl.[5] ..... A01H 5/00

[52] U.S. Cl. ..... Plt./51

[58] Field of Search ..... Plt. 51, 53.3

[56] References Cited

U.S. PATENT DOCUMENTS

P.P. 5,554 9/1985 King ..... Plt. 53.3

*Primary Examiner*—Howard J. Locker

*Attorney, Agent, or Firm*—Christie, Parker & Hale

[57] ABSTRACT

A new variety of Chinese Elm having unusual yellow leaf coloring.

2 Drawing Sheets

SUMMARY OF THE INVENTION

The present invention relates to a new and distinct variety of Chinese Elm (*Ulmus parvifolia*), sometimes referred to as "Lace Bark Elm". The varietal denomination of the new elm is "Golden Rey Elm".

The variety "Golden Rey Elm" was discovered by me in a controlled planting of seedlings of Chinese Elm Trees in Oklahoma City, Ok. The unusual and distinct color of the new leaves indicated that this was a new and distinct variety. After growing and observing the original tree seedling, the variety was asexually propagated by grafting onto one-year seedlings of species *Ulmus parvifolia.* Additional asexual reproduction was made by rooting cuttings of the new variety under an intermittent mist system. It was observed that the cuttings rooted in approximately 45 days in early summer. Asexual reproduction of the new variety shows that the following and other distinguishing characteristics of the variety come true to form and are established and transmitted through succeeding propagations.

The variety "Golden Rey Elm" is distinguished by the color of the new leaves which are a very uniform light yellow coloring that changes to near chartreuse yellow when attaining full size and maturity. Leaves out of direct sunlight tend toward a light green coloring. In the autumn, the natural coloring deepens until leaf drop when all the leaves tend to be a deeper shade of summer color, which in overall tonality appears as golden yellow. In central Oklahoma, abscission normally occurs in November.

The growth rate of the new variety is believed to be similar to the species which, under normal nursery conditions, is about two to three feet per growing season. Overall growth is upright when young but becoming more rounded with age so that the mature shape is a broad, rounded configuration with ends of the new growth being slightly pedulous. The estimated height at maturity is about 40–60 feet with a width of about one-half to two-thirds of the tree's height. The new variety tends to be more compact, with more branches, and of more upright form than the species at comparable maturity.

The bark on young trees of the new variety, i.e., up to 5–6 years of age, appears to be a uniform brownish grey. At approximately this age, the bark begins to exfoliate and develops splotches of light tan where portions of older bark have fallen away. This behavior is similar to that of the species.

Observed under field growing conditions, the disease resistance of the new variety seems to be equal to that of the species. The species *Ulmus parvifolia* is considered one of the most disease and insect resistant trees in the elm group.

BRIEF DESCRIPTION OF THE DRAWING

The accompanying photographic illustrations show specimen trees of the new variety in coloration during the growing season depicted as true as it is possible to make in a color illustration of this character. Sheet 1 shows a row of trees and the new variety of approximately three years of age and Sheet 2 shows a specimen of the new variety at approximately 6–7 years of age.

The following description and particular leaf characteristics and the information in Table I have been observed from specimens of the new variety grown in Oklahoma City, Ok. in the month of September. The color designations referred to herein are from The Horticultural Color Chart (H.C.C.) distributed by the British Color Counsel, London. For reference, where possible corresponding color values from The Royal Horticultural Society Colour Chart (R.H.S.C.C.) are also provided with reference to the accompanying photographic illustrations.

As indicated previously, the distinguishing feature of the new variety, "Golden Rey Elm", is the yellow coloring of the leaves that persists from early spring until the leaves drop in the autumn. The color of the new leaves tends to be very uniform, near primrose yellow (H.C.C. 601/1) (R.H.S.C.C. near 4A to 4B) which changes to near chartreuse yellow (HCC 663/1) (R.H.S.C.C. near 154B) when the leaves mature. Leaves maintained out of direct sunlight tend to produce a light green coloring nominally referred to as "lettuce green". In the autumn, the color of the yellow leaves deepens until the leaves drop at which time the leaf coloring tends to be a deeper shade of the summer coloring which can be described in overall tonality of golden yellow.

Table I

1. Petiole length: 4 mm.
2. New leaves are near primrose yellow H.C.C. 601/1 (near R.H.S.C.C. 4A to 4B).

3. Mature leaves are near chartreuse green H.C.C. 663/1 (near R.H.S.C.C. 154B).
4. Older leaves out of the sun are lettuce green, near H.C.C. 861 (near R.H.S.C.C. 144A).
5. Average leaf length is 4 to 6 cm, not including petiole.
6. Average leaf width is 2.5 to 3 cm at the widest point.
7. Leaf shape is similar to that of the species and is described in the Manual of Cultivated Trees by Alfred Rehder which is specifically incorporated herein by reference.
8. Leaves are elliptic to ovate, unequally rounded at the base, simply or nearly simply serrate, lustrous and smooth above on mature leaves, with young leaves being scabrous to the touch, less so on mature trees.

The distinctive features of the new variety, including the bright yellow coloring of the leaves in the growing season and the compact, upright growth, make the "Golden Rey Elm" an especially useful tree for landscaping.

I claim:

1. A new and distinct variety of *Ulmus parvafolia* substantially as shown and described, characterized by unusual and attractive yellow coloring of leaves that persists from early spring until the leaves drop in the autumn.

* * * * *

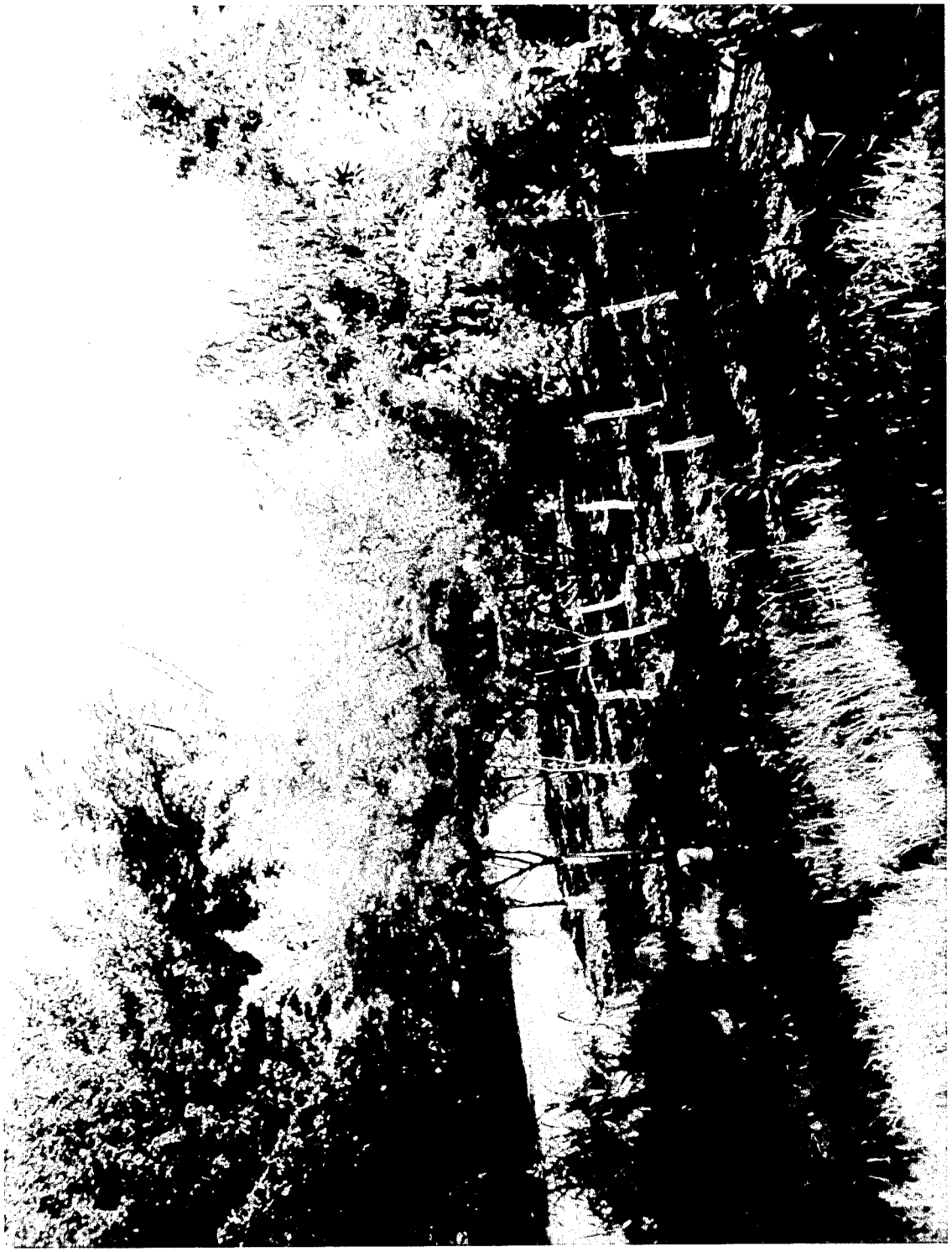

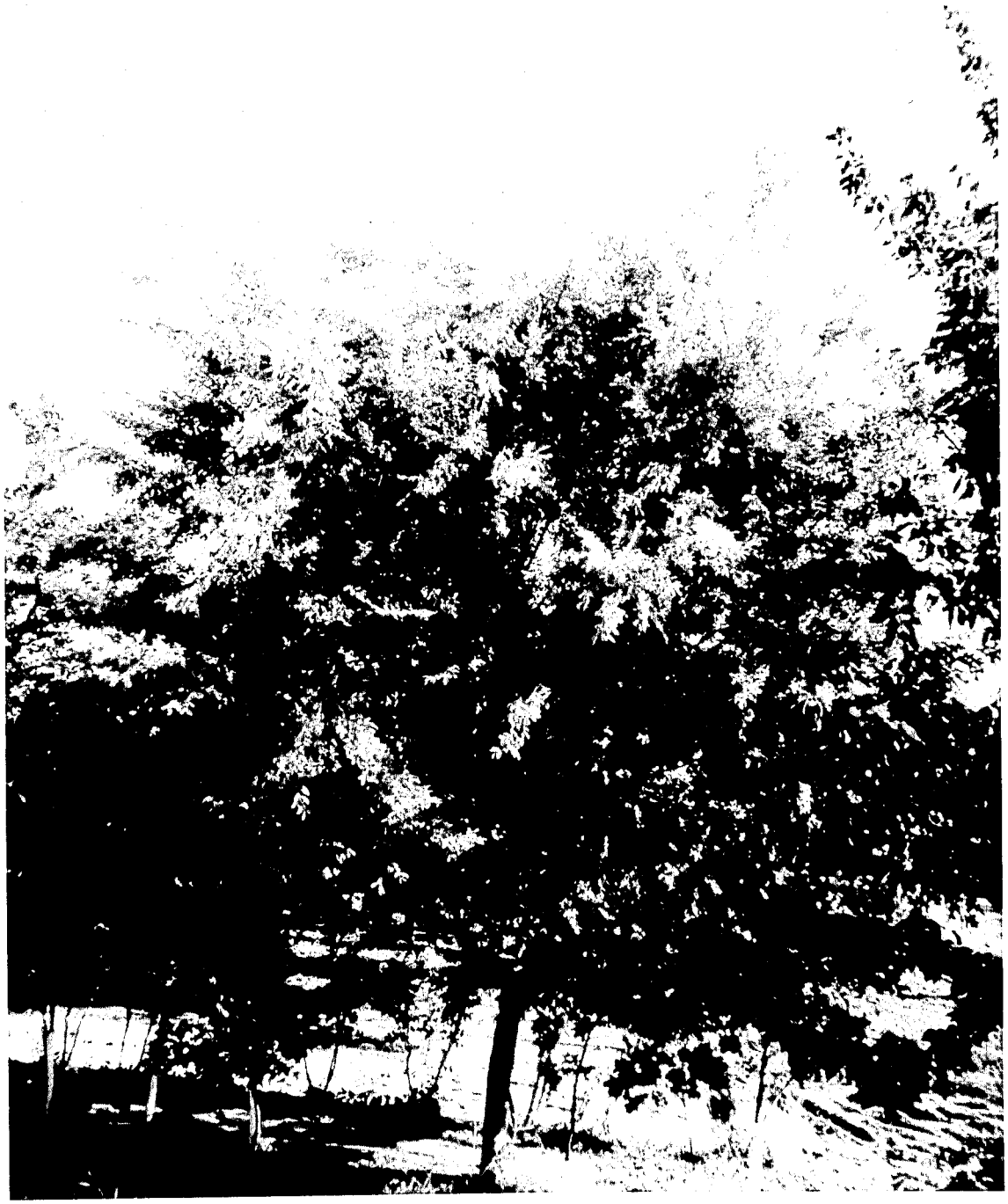

UNITED STATES PATENT AND TRADEMARK OFFICE

CERTIFICATE OF CORRECTION

PATENT NO. : Plant 7,240

DATED : June 5, 1990

INVENTOR(S) : Bruce Rey

It is certified that error appears in the above-identified patent and that said Letters Patent is hereby corrected as shown below:

Column 1, line 20, change "following" to -- foregoing --.

Column 1, line 29, before "summer" insert -- the --.

Column 1, line 39, change "pedulous" to -- pendulous --.

Signed and Sealed this

Twenty-seventh Day of August, 1991

*Attest:*

HARRY F. MANBECK, JR.

*Attesting Officer*

*Commissioner of Patents and Trademarks*